United States Patent [19]

Curtis

[11] 4,067,696

[45] Jan. 10, 1978

[54] BLOOD OXYGENATOR

[75] Inventor: Robert Mark Curtis, Laguna Niguel, Calif.

[73] Assignee: Swiley Laboratories, Inc., Santa Ana, Calif.

[21] Appl. No.: 655,039

[22] Filed: Feb. 3, 1976

[51] Int. Cl.² .............................................. A61M 1/03
[52] U.S. Cl. ........................ 23/258.5 B; 23/258.5 BH; 128/DIG. 3; 195/1.8; 261/76; 261/94; 261/122; 261/DIG. 28
[58] Field of Search ................. 23/258.5 B, 258.5 BH; 261/76, 94–98, 122, 123; 128/DIG. 3; 195/1.8

[56] References Cited

U.S. PATENT DOCUMENTS

| | | | |
|---|---|---|---|
| 2,771,998 | 11/1956 | Holden | 261/76 X |
| 2,833,279 | 5/1958 | Gollan | 23/258.5 B |
| 3,171,820 | 3/1965 | Volz | 261/94 X |
| 3,322,411 | 5/1967 | Moore | 261/96 |
| 3,388,868 | 6/1968 | Watson et al. | 261/DIG. 26 |
| 3,468,631 | 9/1969 | Raible | 23/258.5 BH |
| 3,547,591 | 12/1970 | Torres | 23/258.5 B |
| 3,769,163 | 10/1973 | Brumfield | 23/258.5 BH |
| 3,827,860 | 8/1964 | Burlis | 23/258.5 B |
| 3,870,470 | 3/1975 | Yoshida et al. | 23/258.5 BH |
| 3,898,045 | 8/1975 | Bowley | 23/258.5 BH |

FOREIGN PATENT DOCUMENTS

| | | | |
|---|---|---|---|
| 1,089,125 | 9/1960 | Germany. | |
| 302,125 | 6/1971 | U.S.S.R. | 23/258.5 B |

Primary Examiner—Barry S. Richman
Assistant Examiner—Michael S. Marcus
Attorney, Agent, or Firm—Knobbe, Martens, Olson, Hubbard & Bear

[57] ABSTRACT

A blood oxygenator wherein blood and oxygen are admixed by flowing blood, into which has been introduced bubbles of oxygen, through a three dimensional, open cellular mixing material having a substantial void volume. In one embodiment, the admixing chamber is provided by an upright cylinder having an open interior. In a second embodiment, the chamber has an annular interior configuration. In both embodiments, the open cellular mixing material completely fills the cross-sectional interior of the chamber. The resulting arterialized blood and blood foam rise to the top of the admixing chamber and are contained in a channel located at the top of the chamber and directed through this channel to the input of a defoamer chamber. A defoamer filter of annular configuration is retained within the defoamer chamber such that the defoamer inlet is located at the top of the defoamer filter within the interior annular space thereof. The blood foam thus enters the interior of the defoamer filter and is distributed over a substantial portion of the defoamer surface and collapsed therein to remove all entrapped gases. The oxygenated defoamed blood collects at the bottom of the defoamer chamber for return to the patient's body.

24 Claims, 8 Drawing Figures

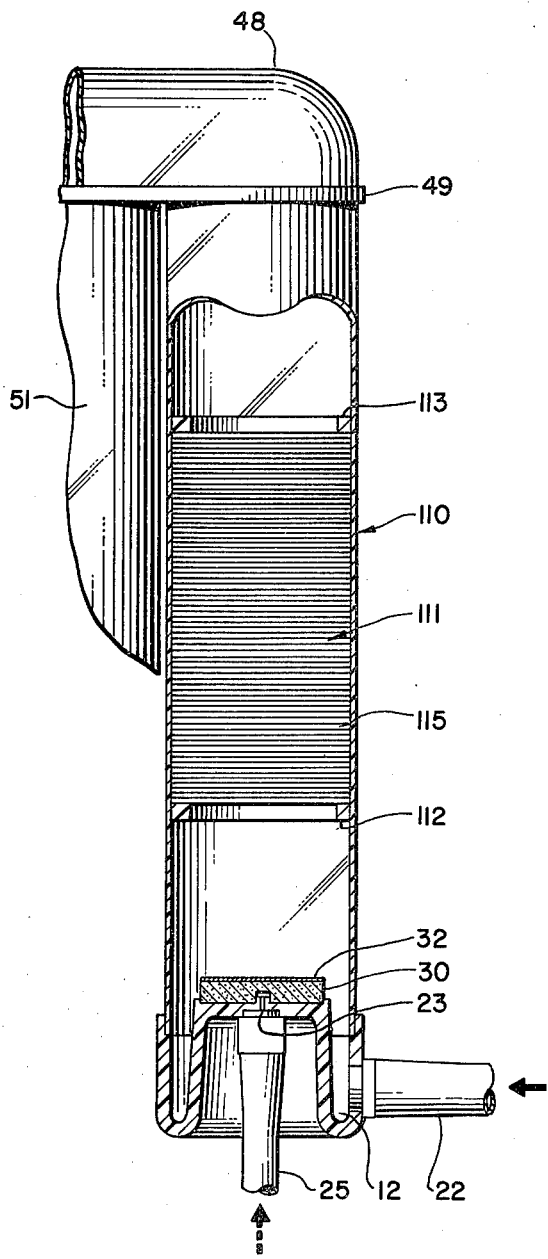
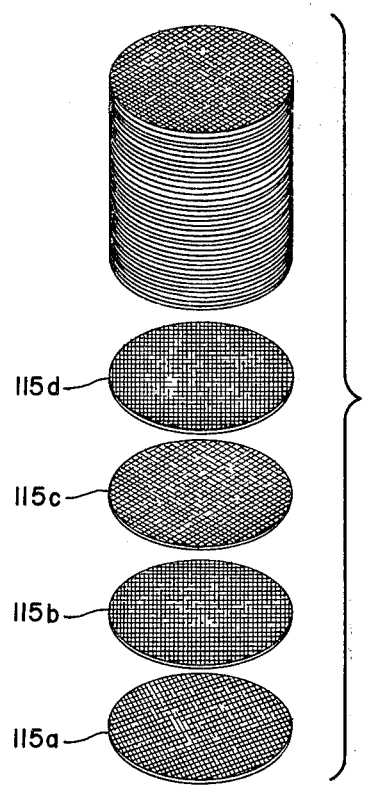
FIG. 7.
FIG. 8.

BLOOD OXYGENATOR

BACKGROUND OF THE INVENTION

Extracorporeal circulation is and has been a routine procedure in the operating room for several years. An important component in providing extracorporeal circulation is the blood oxygenator. The function of the oxygenator is to place oxygen in close relationship to the venous blood such that the oxygen reacts with the hemoglobin with resultant absorption of the oxygen and release of carbon dioxide. For an interesting historical survey of blood oxygenators see the article published in the December, 1961 issue of Surgery entitled "Theme And Variations Of Blood Oxygenators" by Richard A. DeWall, M.D. et al.

Three principle types of blood oxygenators are known in the art:

1. In the membrane oxygenator, a membrane separates the blood from the oxygen and gas exchange takes place by diffusion through the membrane. One type of membrane oxygenator is described in U.S. Pat. No. 3,413,095 — Bramson.

2. A film oxygenator exposes a thin film of blood to an oxygen atmosphere. One type of film oxygenator is described in the Dec. 15, 1956 issue of *The Lancet*, page 1246 in the article entitled "Design Of An Artificial Lung Using Polyvinyl Formal Sponge".

3. The bubble oxygenator introduces bubbles of oxygen directly into the blood. In the bubble oxygenator described in U.S. Pat. No. 3,578,411, the bubble chamber has a continuous convoluted path to promote the intermixing of the blood and oxygen. U.S. Pat. No. 3,807,958 describes a bubble oxygenator which employs a plurality of vertical tubes through which the blood and oxygen mixture rises in a slug flow. U.S. Pat. No. 3,898,045 describes a bubble oxygenator having a lattice chamber tightly packed with spherical beads to provide what the patentee describes as a "wiped film bubble oxygenation process". In still another type of bubble oxygenator described in an article published in Surgery, August, 1957 entitled "Preliminary Studies On The Sponge-Oxygenator" by Adriano Bencini, M.D. et al, a long multi-perforated needle is inserted into a cylindrical piece of polyurethane sponge.

SUMMARY OF THE INVENTION

The present invention relates to an improved type of "sponge" oxygenator as taught by Dr. Bencini et al, supra.

In the preferred embodiment as described hereinafter, the admixing chamber is formed by an upright plastic cylinder. The blood and oxygen are introduced at the bottom of this cylinder, the blood flowing into an annular cavity formed by an end cap member and the oxygen flowing through a sparger which creates oxygen bubbles through the blood. This venous blood into which the bubbles of oxygen gas have been introduced flows upwardly through a three dimensional, open cellular mixing material having a substantial void volume completely filling the open cross-sectional area of the admixing chamber along the length of the mixing material. This mixing material thoroughly mixes the gaseous oxygen and liquid blood phases and produces a large quantity of blood foam. As a result, $CO_2$ is removed from the blood and the blood is saturated with oxygen.

The arterialized blood and blood foam flow out of the top of the admixing chamber and are contained in a channel connected to the inlet of a defoamer chamber. The defoamer chamber likewise advantageously comprises a second upright plastic cylinder having mounted therein an annular defoamer filter. As a result, a substantial portion of the interior cavity wall surface of the defoamer filter is contacted by the arterialized blood and blood foam. The defoamer filter collapses the bubbles in the blood such that the entrapped gases escape through openings formed in the defoamer chamber. The arterialized whole blood falls to the bottom of the defoamer chamber from which it is returned to the patient.

A significant feature of this invention is that it requires a low rate of oxygen flow, i.e. saturation of the blood with oxygen and the concomitant removal of $CO_2$ are achieved with a low volumetric ratio of oxygen to blood. Thus, certain types of bubble oxygenators in wide usage require between two and two and one-half liters of oxygen for each liter of venous blood at atmospheric pressure. The present invention operates very efficiently and satisfactorily on approximately 1 liter or less of gas to one liter of blood ratio at atmospheric pressure. Such a low rate of oxygen flow is deemed important because published technical papers report that the degree of blood trauma in bubble oxygenators can be related to the volumetric ratio of oxygen to blood.

Although all aspects of the improved blood oxygenation provided by the invention are not presently known, it is believed that one reason that oxygen saturation and $CO_2$ removal are achieved with a relatively low rate of oxygen flow is that the mixing and churning of the blood and bubbles of oxygen within the three dimensional open cellular mixing material produces a substantial disturbance to the diffusion boundary layers occurring at the surfaces of the oxygen bubbles. This mixing activity is further enhanced in that the oxygen bubbles are broken down in size and forced to take tortuous paths through the blood. The thorough mixing of blood and oxygen bubbles achieved in this invention is physically manifested by the production of large numbers of small bubbles, the mixture of blood and bubbles exhibiting a foam like behavior and referred to below as blood foam. As described hereinafter, oxygenators constructed in accordance with this invention effectively channel and collapse all of the foam produced during admixing of the blood and oxygen.

The conventional teaching of the prior art in the field of bubble and other types blood oxygenators as exemplified by the paper of Dr. Bencini et al, supra, was that blood foaming should be avoided or at least minimized. The present invention is therefore a substantial departure from and quite distinctive over the prior art blood oxygenator including both bubble and film type devices since the present invention is designed to and does promote the formation of blood foam. Extensive animal testing of bubble oxygenators constructed in accordance with this invention employing standard oxygenator test procedures prove that the invention achieves saturation of the blood with oxygen and removal of $CO_2$ therefrom with significantly low rates of oxygen flow while maintaining the blood integrity to the same or higher standards as contemporary bubble oxygenators.

A correlative advantage of the admixing chamber of the present invention is that the mixing material therein advantageously has a substantial void volume. As a result the blood is not required to pass through any constricted spaces. The admixing chamber is therefore a low impedance to the flow of blood and in addition the blood flow velocity within the admixing chamber is kept low. As a result, no positive pressure source and only gravity feed from the patient is required on the venous inlet side of the device.

Other features of the invention are that it is sufficiently inexpensive to manufacture such as that it can be a disposable item thereby avoiding any necessity to sterilize the unit after use. The individual components of the oxygenator are easily and inexpensively manufactured from materials which are biologically inactive and compatible with human blood.

BRIEF DESCRIPTION OF THE DRAWINGS

FIG. 7 is a sectional view of an alternative embodiment of the oxygenator chamber utilizing a multiple layer foraminous member; and FIG. 8 is a partially exploded view in perspective of the multiple layer foraminous admixing member shown in the embodiment of FIG. 7.

DETAILED DESCRIPTION OF THE INVENTION

Figure 1:
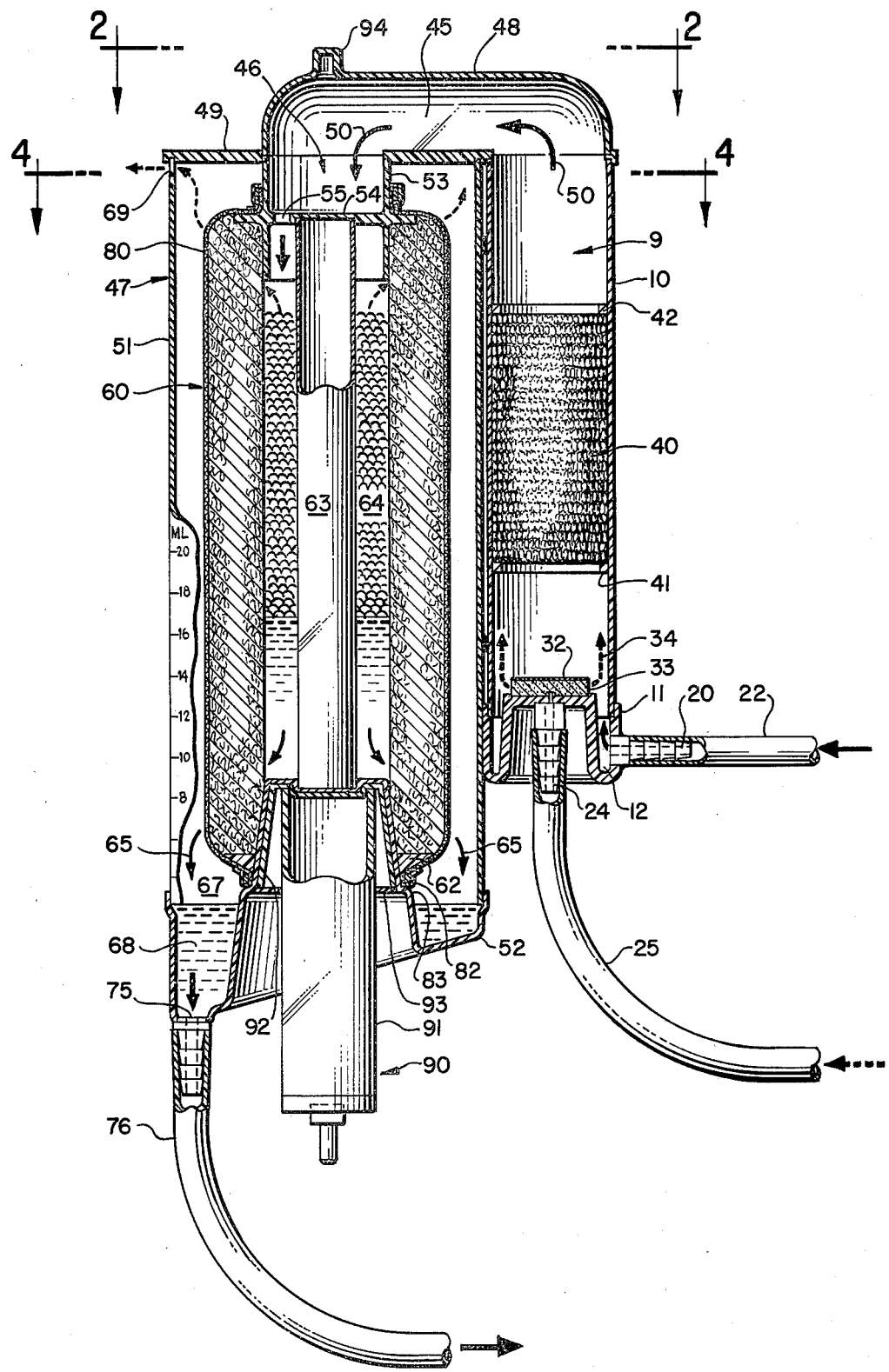
FIG. 1 is a vertical elevational partial sectional view of a blood oxygenator constructed in accordance with the present invention.
Figure 2:
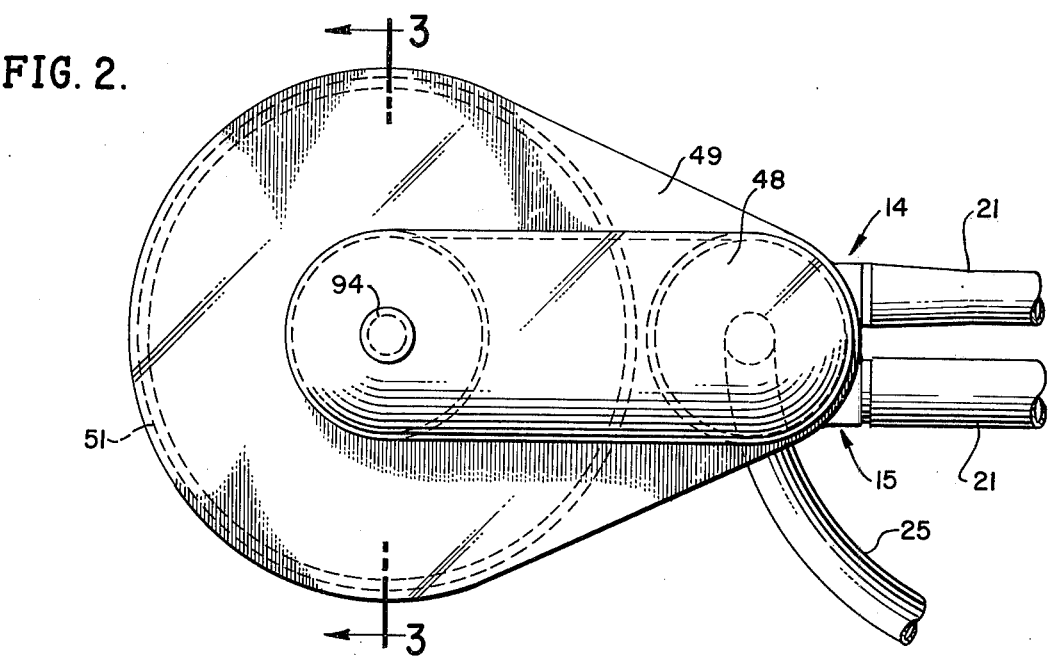
FIG. 2 is a top elevational view of the blood oxygenator.
Figure 3:
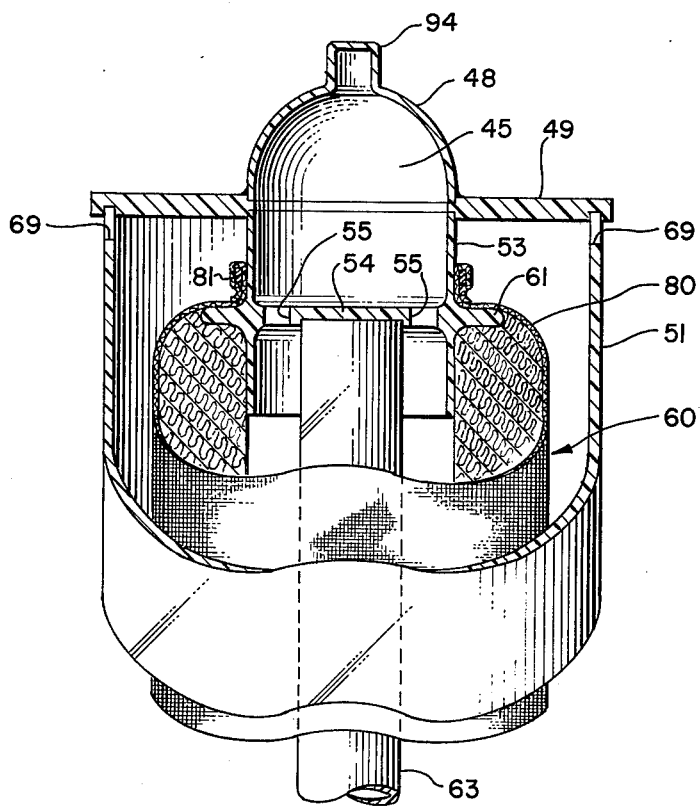
FIG. 3 is a partially sectional view taken along the line 3—3 of FIG. 2 and shows the internal construction of the defoamer filter.
Figure 4:
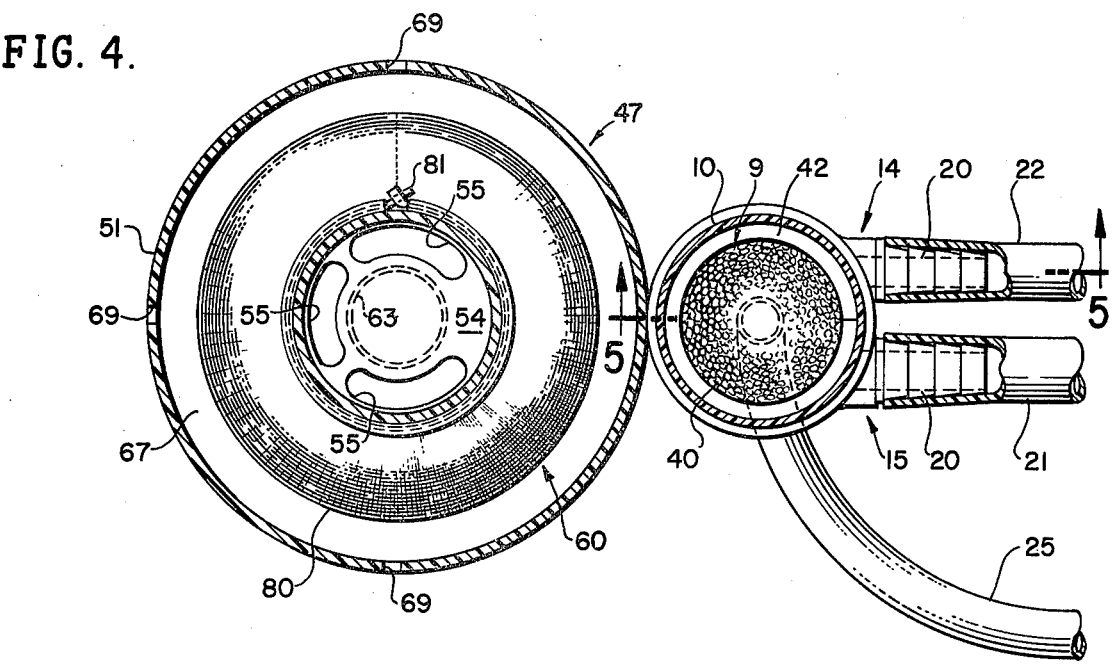
FIG. 4 is a horizontal sectional view taken along the line 4—4 of FIG. 1 and shows structural details of the admixing chamber and the defoamer filter.
Figure 5:
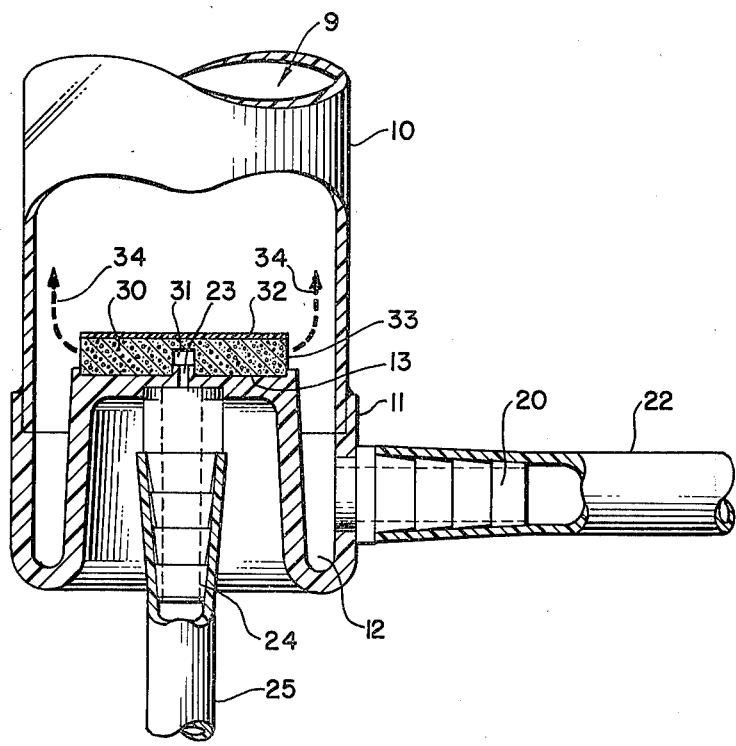
FIG. 5 is an enlarged partially sectional view taken along the line 5—5 of FIG. 4 and shows the details of the oxygen and venous blood inlets and sparger assembly.

Referring now to FIGS. 1-5, the blood oxygenator includes an oxygenating chamber 9 for thoroughly admixing blood and oxygen. In the embodiment shown, this chamber 9 is formed by a cylindrical shell 10 having its lower end closed off by a multi-port end cap 11. As particularly shown in FIG. 5 this end cap is configured to form an annular interior trough 12 surrounding a raised horizontal surface 13. In the outer wall of the end cap 11 are formed one or more blood inlet ports. As shown in FIGS. 2 and 4, two such ports 14, 15 are advantageously provided one to be connected to a venous drain from the patient and the other to be connected to a cardiotomy reservoir supplied with blood evacuated from the surgical site. Each of these ports 14 and 15 advantageously includes a ridged inlet connector 20 for facilitating attachment to the flexible venous blood conduits 21 and 22. In the center of the cap 11 and extending through the horizontal wall 13 is an oxygen inlet port 23 also advantageously including an outwardly extending ridged connector 24 for attachment to a flexible oxygen line 25.

In use, venous blood enters the ports 14, 15 under a sufficient head of pressure to cause the blood to flow through the oxygenator. Typically this pressure is provided by mounting the entire oxygenator assembly below the patient.

The oxygen entering the inlet port 23 is advantageously caused to form a plurality of oxygen bubbles by means of a sparger 30 which advantageously comprises a solid disc of Tegraglas, a material formed from a multiple of densely packed glass beads of the order of 0.040 cm in diameter and available from the 3M Company. A central plenum chamber 31 is formed in the underside of the sparger disc 30 in communication with the port 23 and a coating 32 of sealant is applied to the top surface of the disc as shown in FIG. 3. As a result, oxygen under pressure flows through the conduit 25, connector 24 and inlet port 23 through the multiple minute spaces provided by the closely packed glass beads to form a multiplicity of oxygen bubbles flowing out of the outer circumferential perimeter 33 of the sparger disc 30 along generally horizontal axes. These bubbles, represented by the arrows 34, flow through the venous blood entering the annular trough 12. This blood, being under pressure, rises inside the chamber 10.

Other means known in the art for forming oxygen bubbles may be used instead of the sparger 30. Moreover, the size of the bubbles produced is not critical as the bubbles are broken down in size during the admixing process. Thus, while the Tegraglas sparger used in the animal tests described below produced bubbles having diameters of the order of 0.3 to 0.5 cm, larger and smaller bubble sizes may be employed in the oxygenator of this invention.

The venous blood and oxygen bubbles are thoroughly admixed as they flow through a three dimensional, open cellular mixing material 40 supported above the sparger 30 within the chamber 9 and completely filling the cross-sectional interior of the chamber along the length of the mixing material 40. The open cellular material 40 produces substantial mixing and churning together of the blood and oxygen bubbles. This mixing and churning disturbs the diffusion boundary layers which exist at the surfaces of the oxygen bubbles to facilitate the reaction of the oxygen with the blood hemoglobin. In addition, the mixing material 40 breaks down the bubbles produced by the sparger 30 and forces these bubbles to follow tortuous paths through the blood. It has been found that this admixing process provides an excellent and thorough admixing of the blood and oxygen and produces blood foam which emerges at the top of the open cell material 40. The open cellular material 40 is retained within the chamber 9 by a pair of annular rings 41 and 42 attached to the inner wall of the shell 10. The degree to which the blood and oxygen are admixed is dependent upon several factors including the degree to which the blood is foamed, the thickness of the blood film forming the foam, and the residence time of the blood foam in the presence of oxygen. By way of specific example, a reticulated polyurethane foam material may be advantageously used as the open cell material 40. The type of blood foam produced by the reticulated polyurethane foam material can be selectively varied by choosing the mesh size of the foam material. The residence time of this blood foam is determined by the pore size and the length of the foam material 40. Excellent saturation of the blood with oxygen and removal of $CO_2$ can be achieved using foam materials having a pore size in the range of 5 to 35 pores per inch and varying the overall material length to maintain the necessary residence time. The reticulated foam has a very substantial void volume, typically 85 to 97% of the total volume, providing an admixing chamber which offers a low impedance to the flow of blood and low blood velocities therewithin. In the animal experiments described below, the oxygenator chamber 10 had an inside diameter of 2 inches, a wall 9 inches long, and a wall thickness of 0.060 inches. The reticulated polyurethane foam material 40 had 10-15 pores per inch and was 2 inches in height. Since substantial blood foaming within the oxygenating chamber 9 has been found to be a desirable function of the mixing material 40, the reticulated polyurethane foam is advantageously not treated with an antifoam compound.

The arterialized blood in the form of liquid blood and blood foam rises to the top of the chamber 10 and is contained in a channel 45 extending from the open top end of chamber 10 to the inlet 46 of the defoamer 47. Channel 45 is formed by a generally half cylindrical shell 48 secured to a flat cover plate 49. This flow path of the arterialized blood and blood foam is represented by the arrows 50 shown in FIG. 1, the arterialized blood and blood foam flowing generally horizontally through the channel 45 and downwardly into the defoamer 47. Defoamer 47 includes a cylindrical shell 51 adjoining the oxygenator shell 10. The top end of shell 51 is enclosed with the cover plate 49 and its bottom end is enclosed by a cap 52 having generally the shape of an inverted cup.

The inlet 46 of the defoamer 47 is formed by a generally cylindrical member 53 secured at its upper end to the cover plate 49 and open to the channel 45. As best shown in FIGS. 3 and 4, the fluid path through member 53 is partially interrupted by a disc 54 formed orthogonal to the axis of cylinder 53. As shown in FIG. 4, disc 54 includes three arcuate apertures 55 spaced from the center of the disc 54 such that both the center portion and the portion of the disc 53 nearest the oxygenating chamber 10 are closed. As described below, the open and closed portions of th disc 54 appropriately channel the arterialized blood and blood foam into the defoamer.

Member 53 and bottom end cap 52 also serve to support an annular defoamer filter 60. Member 53 includes an annular flange 61 over which is secured the upper end of the defoamer filter 60 (FIG. 3) and the bottom end cap 52 has a shaped annular ring 62 under which is secured the bottom end of the defoamer filter 60. A cylindrical column 63 extends between member 53 and bottom end cap 52 inside the defoamer filter 60. The respective ends of this column 63 are sealed to the member 53 and end cap 52 so that the blood flow path is completely external to the column 63. Column 63 provides additional structural rigidity and improved flow through the defoamer filter 60.

The arterialized blood and blood foam represented by arrows 50 flows through the apertures 55 into the interior annular space 64 bounded by column 63 and defoamer filter 60. The bottom of this annular space is sealed by the interior wall of the end cap 62. In use, the blood and blood foam concentrate in the portion of the inlet 46 which is nearest to the oxygenating chamber 9. In order to prevent the blood and blood foam from contacting only a limited portion of the interior wall surface of the defoamer filter, the portion of disc 54 nearest to the oxygenating chamber is closed, as shown in FIGS. 1 and 4. As a result, the blood and blood foam is more evenly distributed by the spaced arcuate apertures 55 around the entire circumference of the interior wall surface of the defoamer filter.

The majority of the liquid blood entering the interior annular space 64 is guided by the column 63 to fill up the bottom of the space 64. This liquid blood flows through the defoamer filter 60 as generally shown by arrows 64. The blood and blood foam enter at the upper end of the defoamer filter 60 so that a substantial portion of the interior wall surface of the filter 60 is contacted by the blood foam. As a result, a substantial portion of the defoamer filter 60 is used to separate the blood foam from the entrapped gas such that the foam collapses and fluid blood flows into the annular reservoir 67 between the filter 60 and the interior wall of the defoamer chamber 51 and settles at the bottom of the chamber 51 and in the end cap 52 as shown at 68. The entrapped gases — primarily oxygen and $CO_2$ — which the defoamer filter 60 separates out are represented by arrows 65 and pass out of the defoamer chamber 51 through three vents 69 (FIG. 4) located near the upper end of this chamber. As a result, only whole liquid blood collects in the space 67. This oxygenated filtered whole blood passes through an outlet port 75 located in the lowermost portion of the end cap 52 and is returned to the patient via flexible arterial conduit 76.

The defoamer filter 60 is advantageously formed from a flat sheet of foam material having a pore size of 10 to 50 pores per inch and typically of the order of one inch thick treated with a thin film of silicone composition. The sheet is folded along its center line and the two ends brought together. This member is then turned inside out to form the annular filter 60 shown in the drawings. This annular filter is covered with a fine weave filter cloth 80, one end of the filter cloth being secured around cylindrical member 53 above flange 61 by a plastic tie 81. The bottom portion of the filter cloth is likewise secured by a plastic tie 82 within the annular indentation formed by the annular ring 62 and a projecting ridge 83 formed in the end cap 52. Ties 81 and 82 also serve to physically secure the annular filter 60 to the member 53 and cap 52. Filter cloth 80 insures that any accumulated blood fragments, particles, etc. in the blood are prevented from entering the annular reservoir 67.

The volume of the defoamer filter should be capable of collapsing the foam produced during (i) the highest ratio of blood and oxygen flow used during a perfusion and (ii) the maximum possible time period of the perfusion procedure. By way of specific example, in the animal experiments described below, the defoamer was constructed from a sheet of polyurethane foam one inch thick having 20 pores per inch. This sheet was formed into an annulus 10½ inches long supported in a cylindrical shell 51 which was 5 inches in diameter, 12 inches long, and had a wall thickness of 0.060 inches. The internal column 63 had an outside diameter of 1 inch.

In use, the blood oxygenator is initially primed with whole blood to compensate for the volume of blood withdrawn from the patient and maintained in circulation ex vivo during the bypass procedure. As described below, the shell 51 is advantageously formed from a clear plastic material. A graduated scale on the side of the shell 51 as shown in FIG. 1 thus permits a precise amount of priming blood to be added. In addition, the amount of blood in the defoamer may be visually monitored at all times so that both excessive or insufficient blood levels in the system may be avoided.

A mounting pedestal 90 includes as shown in FIG. 1 a vertical column 91 secured to the bottom of a cup-shaped member 92 which fits into the upwardly extending portion of the end cap 52. Column 91 extends through a central aperture of a disc 93 whose perimeter is secured to the bottom edge of the cup-shaped member 92. Pedestal 90 may be in turn attached to a mounting bracket (not shown). An additional mounting bracket (not shown) may be attached to a nib 94 formed in the upper wall of the member 48.

Figure 6:
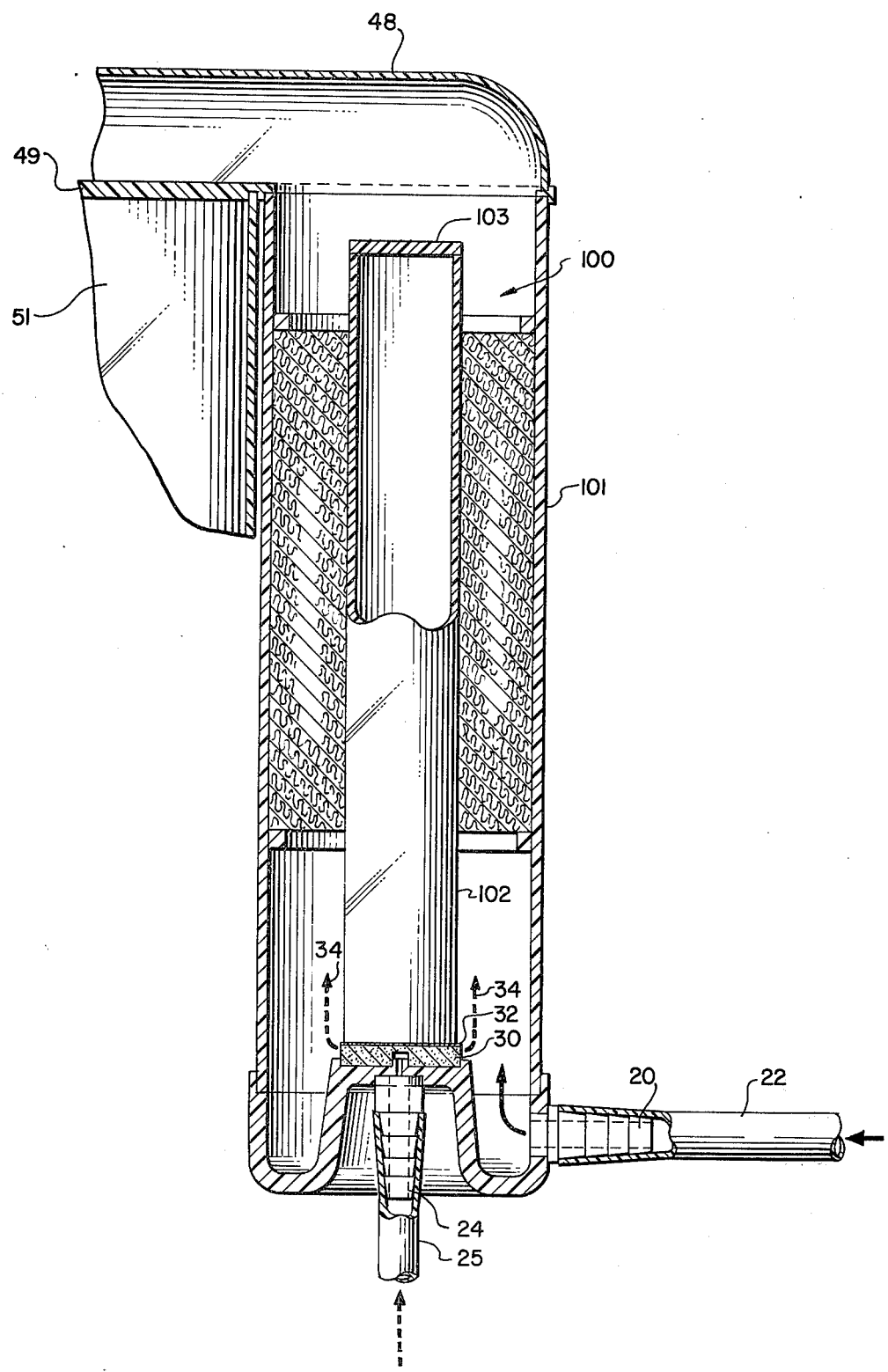
FIG. 6 is a sectional view of a modified admixing chamber which incorporates an interior cylindrical column to form an annular admixing chamber.

A modified embodiment of the oxygenator chamber is shown in FIG. 6. An oxygenating chamber 100 generally larger in diameter than the chamber 9 described above and illustrated in FIGS. 1-5 is provided by an upright cylindrical shell 101 in which is coaxially mounted a column 102. The column 102 is sealed at the top end by disc 103 and at the bottom end by attachment to the sealant coating 32 of sparger 30. Reticulated foam 104 is formed in an annular configuration around the column 102 so as to completely fill the cross-sectional annular space between the column 102 and the inside wall of the cylindrical shell 101. The volume of foam material within this modified oxygenator chamber may be made equivalent to that of the open chamber 9 of FIG. 1 by increasing the diameter of the shell 101 and/or by increasing the length of the foam material. Except for this modification to the oxygenating chamber, the remainder of the blood oxygenator is identical to that of the oxygenator described above and shown in FIGS. 1-5.

An alternative embodiment of the oxygenator chamber is shown in FIGS. 7 and 8. The chamber 110 may be identical in configuration to the chamber 9 of FIG. 1. The venous blood and oxygen bubbles within chamber 110 flow through an open cell, multiple layer foraminous member 111 having a substantial void volume supported between a pair of annular rings 112, 113. Member 111 is advantageously constructed by mounting a plurality of foraminous discs 115 formed from fine mesh plastic screen. As shown in FIG. 8, the axial orientation of the orthogonal plastic strands in each of the discs 115a, 115b, 115c and 115d are displaced one from the other so as to force the oxygen bubbles to follow tortuous paths through the blood. This structure also causes the oxygen bubbles to break down in size thereby providing for a thorough admixing of the oxygen and blood and production of blood foam.

The blood oxygenator of this invention may be inexpensively constructed from materials physiologically compatible with the blood. Thus, the oxygenator and defoamer cylindrical shells, end caps, and structural members in the interior of the defoamer chamber may be extruded or molded from clear polycarbonate. These members may be bonded together by known techniques including cement heat sealing, etc.

The blood oxygenator described above and illustrated in FIGS. 1-5 has been successfully used in several animal tests to maintain blood oxygen levels while the test animal was substantially paralyzed to prevent spontaneous ventilation through his own lungs. By way of specific example, on Nov. 13, 1975, a sheep weighing 91 Kg was sedated with Ketamine and kept substantially paralyzed during the entire perfusion. The animal's temperature remained constant at 37° C. during the test procedures. Bypass cannulae were inserted into the jugular vein and carotid artery. The oxygenator bypass tubing and heat exchanger were initially primed with 2000 ml of blood taken from another animal. One liter of blood was added during the test. The data obtained during this test are listed in Table I. At time=1630, the mechanical ventilator was shut off, the oxygenator then supplied the animal's entire demand for oxygenation and $CO_2$ removal for the duration of the perfusion.

TABLE I

| TIME | STATUS | BLOOD FLOW (l/min) | OXYGEN FLOW (l/min) | OXYGEN FLOW (l/min) / BLOOD FLOW (l/min) | $p^H$ | $P_{CO_2}$ (torr) | $P_{O_2}$ (torr) | Hb gm/100cc | %$O_2$ Saturate |
|---|---|---|---|---|---|---|---|---|---|
| 1430 | Prime | — | — | | | | | | |
| 1530 | Partial Oxygenation | 6.0 | 5.8 | .97 | | | | | |
| 1630 | Complete Oxygenation | 5.1 | 3.7 | .73 | | | | | |
| 1700 | 1st arterial blood sample | 5.1 | 3.4 | .67 | 7.35 | 24 | 250 | | 100. |
| | 1st venous blood sample | | | | 7.27 | 26 | 82 | 12.9 | 79.3 |
| 1720 | 2nd arterial sample | 4.5 | 2.2 | .49 | 7.41 | 29 | 180 | | 99.7 |
| | 2nd venous sample | | | | 7.34 | 29 | 80 | 12.9 | 72.5 |
| 1735 | 3rd arterial sample | 5.2 | 1.5 | .29 | 7.32 | 30 | 130 | | 95.5 |
| | 3rd venous sample | | | | 7.42 | 30 | 78 | 12.9 | 70.5 |
| 1750 | 4th arterial sample | 4.8 | 1.5 | .31 | 7.29 | 33 | 136 | | 96.4 |
| | 4th venous sample | | | | 7.22 | 36 | 84 | 12.6 | 70.8 |
| 1810 | 5th arterial sample | 5.1 | 4.3 | .84 | 7.37 | 29 | 370 | | 100. |
| | 5th venous sample | | | | 7.32 | 32 | 88 | 12.5 | 78.2 |
| 1835 | 6th arterial sample | 3.6 | 2.0 | .56 | 7.33 | 32 | 153 | | 97.9 |
| | 6th venous sample | | | | 7.31 | 32 | 70 | 12.4 | 64.2 |
| 1850 | 7th arterial sample | 3.6 | 1.4 | .39 | 7.27 | 35 | 112 | | 90.3 |
| | 7th venous sample | | | | 7.28 | 38 | 64 | 12.3 | 52.4 |
| 1902 | 8th arterial sample | 4.5 | 2.1 | .47 | 7.23 | 30 | 200 | | 100. |
| | 8th venous sample | | | | 7.29 | 35 | 80 | 12.0 | 72.6 |
| 1910 | Off pump | | | | | | | | |

Following a series of tests to verify the operability of the invention of which the preceding test is exemplary, a later series of tests were conducted which included a plasma hemoglobin analysis for measuring the degree of hemolysis caused by the oxygenation. By way of specific example, on Dec. 3, 1975, a sheep weighing 72 Kg. was perfused and the data obtained are listed in Table II.

Tests such as the ones detailed above prove that saturation of the blood and removal of CO is achieved with low rates of oxygen flow. Typically oxygen perfusions using the invention are performed with a volumetric ratio of oxygen to blood of 1:1 or less. Moreover, the degree of hemolysis caused by this invention, as measured by plasma hemoglobin measurements, is quite low, as exemplified by the data in Table II, thus verifying that the blood oxygenator of this invention maintains the blood integrity to comparable or higher standards than the bubble oxygenators in contemporary clinical use.

TABLE II

PART A

| TIME | STATUS | BLOOD FLOW (1/min) | OXYGEN FLOW (1/min) | OXYGEN FLOW / BLOOD FLOW (1/min) | $p^H$ | $P_{CO_2}$ (torr) | $P_{O_2}$ (torr) | Hb gm/100cc | $\%O_2$ Saturate |
|---|---|---|---|---|---|---|---|---|---|
| 1215 | Prime - Pre Bypass | — | — | | 7.37 | 38 | 650 | 8.8 | 100. |
| | Animal - Pre Bypass | | | | 7.41 | 43 | 310 | 10.1 | 100. |
| 1305 | 1st arterial blood sample | 3.0 | 3.0 | 1.0 | 7.39 | 39 | 360 | 10.4 | 100. |
| | 1st venous blood sample | | | | 7.35 | 48 | 67 | | 73.4 |
| 1320 | 2nd arterial sample | 3.8 | 3.4 | .89 | 7.31 | 50 | 129 | | 97.1 |
| | 2nd venous sample | | | | 7.27 | 56 | 55 | 10.6 | 48.9 |
| 1335 | 3rd arterial sample | 3.8 | 4.0 | 1.06 | 7.36 | 43 | 300 | | 100. |
| | 3rd venous sample | | | | 7.38 | 51 | 63 | 10.5 | 64.3 |
| 1348 | 4th arterial sample | 3.8 | 4.7 | 1.3 | 7.39 | 38 | 415 | | 100. |
| | 4th venous sample | | | | 7.33 | 48 | 66 | 10.6 | 68.2 |
| 1405 | 5th arterial sample | 3.8 | 4.7 | 1.3 | 7.41 | 38 | 460 | | 100. |
| | 5th venous sample | | | | 7.34 | 44 | 68 | 10.6 | 70.8 |
| 1430 | 6th arterial sample | 4.0 | 4.0 | 1.0 | 7.41 | 36 | 440 | | 100. |
| | 6th venous sample | | | | 7.34 | 45 | 69 | 10.6 | 69.5 |
| 1450 | 7th arterial sample | 4.1 | 4.6 | 1.1 | 7.40 | 38 | 505 | | 100. |
| | 7th venous sample | | | | 7.36 | 42 | 70 | 10.4 | 72. |
| 1500 | 8th arterial sample | 4.0 | 3.1 | .78 | 7.36 | 41 | 280 | | 99.4 |
| | 8th venous sample | | | | 7.32 | 50 | 68 | 10.6 | 65. |
| 1520 | 9th arterial sample | 3.7 | 3.1 | .84 | 7.35 | 47 | 385 | | 100. |
| | 9th venous sample | | | | 7.28 | 54.3 | 70 | 10.5 | 64.8 |
| 1540 | 10th arterial sample | 3.6 | 3.1 | .86 | 7.35 | 43 | 400 | | 100. |
| | 10th venous sample | | | | 7.29 | 52.5 | 72 | 10.5 | 65.8 |
| 1610 | 11th arterial sample | 3.2 | 2.7 | .84 | 7.32 | 43 | 385 | | 100. |
| | 11th venous sample | | | | 7.26 | 57 | 68 | 10.6 | 61.6 |
| 1630 | 12th arterial sample | 2.9 | 2.7 | .93 | 7.29 | 53.5 | 585 | | 100. |
| | 12th venous sample | | | | 7.29 | 59.3 | 80 | 10.7 | 76.6 |
| 1631 | Off Pump | | | | | | | | |

PART B
PLASMA HEMOGLOBIN ANALYSIS

| SAMPLE | TIME | IDENTIFICATION | PLASMA HEMOGLOBIN mg.% | mg.%/min |
|---|---|---|---|---|
| 1 | Pre Bypass | Animal | <8 | — |
| 2 | Pre Bypass | Prime | 30 | — |
| 3 | ½ hr. | On Bypass | 14 | — |
| 4 | 1 hr. | On Bypass | 15.5 | .05 |
| 5 | 2 hr. | On Bypass | 21.5 | .10 |
| 6 | 4 hr. | On Bypass | 25.8 | .04 |
| 7 | 1 day | Post Bypass | 8 | — |

I claim:

1. A blood oxygenator which requires a low volumetric ratio of oxygen to blood comprising:
an oxygenating chamber;
first means for introducing blood and oxygen into said oxygenating chamber comprising blood and oxygen inlet means therein;
second means coupled to said oxygen inlet means for introducing a plurality of bubbles of oxygen in the blood, said first means providing a site for oxygen bubble formation in the absence of and unimpeded by any means for mixing said blood and oxygen bubbles;
third means so located that said blood and oxygen bubbles flows therethrough downstream of and spaced from said site for bubble formation, said third means mixing and churning together said blood and oxygen bubbles to break down said oxygen bubbles and form blood foam comprising an open cellular mixing material means within said chamber, said mixing material means having a three dimensional body configuration for providing a plurality of tortuous paths so that oxygen bubbles are both broken down and caused to travel in a plurality of tortuous paths through said blood before escaping from said mixing material means, said three dimensional, open cellular mixing means having a void volume substantially larger than 50% so that said oxygenating chamber provides low impedence to the flow of blood therethrough and provides relatively low velocities of blood therein;
an outlet means in said oxygenating chamber through which the oxygenated foamed blood passes; and
defoamer means coupled to said outlet means for defoaming the oxygenated blood.

2. The blood oxygenator of claim 1 wherein said open cellular mixing material means is reticulated polyurethane foam.

3. The blood oxygenator of claim 1 in which said three dimensional, open cellular mixing material means substantially completely fills the cross-sectional interior of said oxygenating chamber along a substantial portion of the length of said oxygenating chamber.

4. The blood oxygenator of claim 1 in which said oxygenating chamber comprises an upright clear cylindrical shell.

5. The blood oxygenator of claim 1 in which a member extends upwardly within said oxygenator chamber, said open cellular mixing material means formed in an annulus around said member so as to substantially completely fill the cross-sectional annular space between said member and the inside wall of the upright oxygenator chamber.

6. The blood oxygenator of claim 1 wherein the pore size of said open cellular mixing material means is in the range of 5 to 35 pores per inch.

7. The blood oxygenator of claim 1 wherein said three dimensional, open cellular mixing material means has a void volume in the range of 85 to 97%.

8. The blood oxygenator of claim 1 wherein said open cellular mixing material means is a multiple layer of foraminous members in juxtaposed position.

9. The blood oxygenator of claim 8 wherein said layers are comprised of juxtaposed plastic screen discs with the axial orientation of the plastic strands of the respective discs being displaced one from the other.

10. The blood oxygenator of claim 1 in which said means for introducing a plurality of bubbles of oxygen in the blood comprises a sparger means having a plurality of very small interstices for generating plural oxygen bubbles, said sparger means being open on its sides and closed on its top and bottom surfaces so that said bubbles are ejected along generally horizontal axes.

11. The blood oxygenator of claim 10 in which said blood inlet means in the lower end of said chamber comprises an annular trough below said sparger, said oxygen bubbles being discharged into the blood as it flows upwardly from said annular trough.

12. The blood oxygenator of claim 11 wherein said sparger means is formed from a solid disc of densely packed glass beads and having its upper surface sealed and its bottom surface attached to a raised horizontal surface surrounded by said annular trough in the lower end of said chamber.

13. The blood oxygenator of claim 1 in which channel means connect the outlet means of said chamber to said defoamer means, said channel means containing all of the blood foam produced in said oxygenating chamber by the mixing and churning together of the blood and oxygen.

14. The blood oxygenator of claim 8 wherein said oxygenating chamber comprises a first upright chamber and said defoamer means is housed in a second upright chamber and said defoamer means is housed in a second upright chamber located adjacent to said first upright chamber and having an inlet opening means in the upper end thereof, said channel means being generally horizontal and located above both said first and second upright chambers and connecting the outlet of said oxygenating chamber with the inlet means of said defoamer chamber whereby the blood and blood foam (a) flow upwardly out of the outlet means in the upper end of said oxygenating chamber into one end of said horizontal channel means, (b) flow generally horizontally from one end to the opposite end of said channel means and (c) flow downwardly from said opposite end of said channel means into the input means of said defoamer means.

15. The blood oxygenator of claim 1 in which said oxygenating chamber comprises a first upright chamber and said defoamer means is housed within a second upright chamber adjoining said oxygenating chamber, an annular defoamer filter supported within said second chamber, a defoamer inlet means into the upper end of said chamber leading to the upper end of the interior of said defoamer filter so that a substantial portion of the interior wall surface of the defoamer filter is contacted by the blood foam, said blood foam being collapsed in said defoamer filter with the entrapped gases passing out of openings in the upper end of defoamer chamber and the whole blood collected in the bottom of the defoamer chamber.

16. The blood oxygenator of claim 15 in which said defoamer inlet means distributes the blood and blood foam around a substantial portion of the interior wall surface of said defoamer filter.

17. The blood oxygenator of claim 15 in which a rigid column extends upwardly within the interior of said annular defoamer filter, said column serving both as a support member and a guide for the liquid blood flowing into said defoamer inlet means.

18. The blood oxygenator of claim 15 in which said defoamer chamber comprises a clear cylindrical shell.

19. A blood oxygenator for admixing blood and oxygen for absorption of oxygen and release of carbon dioxide comprising:
an oxygenating chamber;
first means for introducing blood and oxygen into said oxygenating chamber comprising venous blood and oxygen inlet means therein;
second means coupled to said oxygen inlet means for introducing a plurality of bubbles of oxygen in the venous blood;
third means for producing substantial mixing and churning together of the blood and oxygen bubbles sufficiently to disturb the diffusion boundary layers at the surfaces of the oxygen bubbles to facilitate the reaction of the oxygen with the blood hemoglobin and characterized by the production of blood foam comprising an open cellular mixing material means within said chamber downstream of and spaced from said second means having a three dimensional body configuration through which is flowed substantially all of the venous blood and oxygen bubble mixture for providing a plurality of tortuous paths so that said oxygen bubbles are broken down and caused to travel in a plurality of tortuous paths through said blood before escaping from said mixing material means, said mixing material means having a void volume substantially larger than 50% so that said oxygenating chamber (i) provides low impedance to the flow of blood therethrough, (ii) provides relatively low velocities of blood therein, and (iii) can be gravity fed from the patient without any positive pressure pump between the patient and said blood inlet;
means coupled to said oxygenating chamber for containing the arterialized blood and blood foam produced by said mixing and churning; and
means for defoaming said contained blood and blood foam and producing arterialized whole blood.

20. The blood oxygenator of claim 19 wherein said open cellular mixing material means comprises a reticulated polyurethane foam.

21. The blood oxygenator of claim 19 wherein said open cellular mixing material means is a multiple layer of foraminous members in juxaposed position.

22. A blood oxygenator which requires a low volumetric ratio of oxygen to blood comprising:
a first clear plastic cyclindrical shell having blood and oxygen inlet means in the lower end thereof;
a sparger member supported with said first shell at the lower end thereof and coupled to said oxygen inlet means, said sparger member having a plurality of very small interstices for injecting plural oxygen bubbles into blood flowing into said first shell through said blood inlet means;
a reticulated foam mixing material having a void volume in the range of 85–97% supported within said first cylindrical shell downstream of and spaced above said blood inlet means and sparger member and substantially completely filling the open cross-sectional interior of said first shell along the length of said foam material, said reticulated foam material being free of any anti-foam coating thereon, said blood into which oxygen bubbles have been introduced rising within said shell through said reticulated foam material, said reticulated foam causing said blood and oxygen bubbles to be churned and mixed together sufficiently to disturb the diffusion boundary layers at the surfaces of the oxygen bubbles to facilitate the reaction of the oxygen with the blood hemoglobin, said reticulated foam material having a three dimensional body configuration and a pore size in the range of 5 to 35 pores per inch whereby said oxygen bubbles are both broken down in size and forced to follow a plurality of tortuous paths through said blood;

a second clear plastic cylindrical shell mounted proximate to said first shell and having an inlet means connected to the upper end thereof;

a channel for containing the blood and blood foam emerging at the top of said reticulated foam, said channel connecting the upper end of said first shell to the inlet means of said second shell; and an annular defoamer filter supported within said second shell with the interior of said defoamer filter in communication with the inlet means of second shell, said defoamer filter comprising a reticulated foam material having a pore size in the range of 10 to 50 pores per inch covered with a fine weave filter cloth, all of said arterialized blood and blood foam passing from within the interior of said annular filter to a space between the outer surface of said filter and the entrapped gases pass out of openings in the upper end of said second shell and the whole blood is collected in the bottom thereof.

23. The blood oxygenator of claim 22 wherein a member extends within said first shell and said reticulated foam is formed in an annulus around said member so as to substantially completely fill the cross-sectional interior space between said member and the inside wall of said first shell along a substantial portion of the length of said reticulated foam.

24. The blood oxygenator of claim 22 wherein said sparger member produces bubbles having diameters of the order of 0.3 to 0.5 cm.

* * * * *

UNITED STATES PATENT AND TRADEMARK OFFICE
CERTIFICATE OF CORRECTION

PATENT NO. : 4,067,696
DATED : January 10, 1978
INVENTOR(S) : Robert Mark Curtis It is certified that error appears in the above-identified patent and that said Letters Patent are hereby corrected as shown below:

In the heading under [73] "Swiley" should be --Shiley--

Col. 3, line 53, add --;-- after "provide"

Col. 5, line 38, "th" should be --the--

Signed and Sealed this

Ninth Day of May 1978

[SEAL]

Attest:

RUTH C. MASON
Attesting Officer

LUTRELLE F. PARKER
Acting Commissioner of Patents and Trademarks